United States Patent
Gill et al.

(10) Patent No.: US 11,154,377 B2
(45) Date of Patent: Oct. 26, 2021

(54) NEUROSURGICAL APPARATUS

(71) Applicant: RENISHAW PLC, Wotton-under-Edge (GB)

(72) Inventors: Steven Streatfield Gill, Bristol (GB); Paul Fielder, Stroud (GB); Maxwell Roy Woolley, Bristol (GB)

(73) Assignee: RENISHAW PLC, Wotton-under-Edge (GB)

( * ) Notice: Subject to any disclaimer, the term of this patent is extended or adjusted under 35 U.S.C. 154(b) by 150 days.

(21) Appl. No.: 15/127,536

(22) PCT Filed: Mar. 19, 2015

(86) PCT No.: PCT/GB2015/050798
§ 371 (c)(1),
(2) Date: Sep. 20, 2016

(87) PCT Pub. No.: WO2015/140552
PCT Pub. Date: Sep. 24, 2015

(65) Prior Publication Data
US 2017/0135778 A1    May 18, 2017

(30) Foreign Application Priority Data
Mar. 20, 2014 (GB) ..................................... 1404978

(51) Int. Cl.
*A61B 90/11* (2016.01)
*A61M 25/00* (2006.01)
(Continued)

(52) U.S. Cl.
CPC .......... *A61B 90/11* (2016.02); *A61B 17/3417* (2013.01); *A61M 25/0026* (2013.01);
(Continued)

(58) Field of Classification Search
CPC ........ A61M 39/0247; A61M 2039/025; A61M 2039/027; A61M 2039/0273;
(Continued)

(56) References Cited

U.S. PATENT DOCUMENTS

| 4,973,321 A | * 11/1990 | Michelson ......... A61B 1/00094 600/114 |
| 5,647,846 A | 7/1997 | Berg et al. |

(Continued)

FOREIGN PATENT DOCUMENTS

| EP | 2601997 A1 | 6/2013 |
| JP | 2008-125840 A | 6/2008 |

(Continued)

OTHER PUBLICATIONS

Jun. 15, 2015 International Search Report issued in International Patent Application No. PCT/GB2015/050798.

(Continued)

*Primary Examiner* — Kevin T Truong
*Assistant Examiner* — Tracy L Kamikawa
(74) *Attorney, Agent, or Firm* — Oliff PLC (57) ABSTRACT

Neurosurgical apparatus has a guidance device having a guide tube and a neurosurgical instrument for insertion into the guide tube. The inner surface of the guide tube is arranged, for example profiled, to at least partially engage the outer surface of the neurosurgical instrument when inserted therein. The guide tube thus guides the neurosurgical instrument along a predefined path through the guide tube. At least one of the guidance device and the outer surface of the neurosurgical instrument are configured to provide a fluid return path for carrying any fluid displaced from within the guide tube during insertion of the neurosurgical instrument into the guide tube. A seal may also be provided for sealing the fluid return path.

13 Claims, 5 Drawing Sheets

(51) Int. Cl.
*A61M 25/06* (2006.01)
*A61M 39/02* (2006.01)
*A61B 17/34* (2006.01)
*A61B 90/10* (2016.01)
*A61M 25/02* (2006.01)

(52) U.S. Cl.
CPC .... *A61M 25/0043* (2013.01); *A61M 25/0662* (2013.01); *A61M 39/0247* (2013.01); *A61B 2090/103* (2016.02); *A61M 25/00* (2013.01); *A61M 25/02* (2013.01); *A61M 2025/0042* (2013.01); *A61M 2025/0233* (2013.01); *A61M 2039/025* (2013.01); *A61M 2039/027* (2013.01); *A61M 2039/0273* (2013.01); *A61M 2039/0282* (2013.01); *A61M 2210/0693* (2013.01)

(58) Field of Classification Search
CPC .......... A61M 2039/0282; A61M 25/00; A61M 25/0043; A61M 25/02; A61M 25/0662; A61M 2025/0042; A61M 25/0233; A61M 2210/0693; A61B 90/11; A61B 2090/103; A61B 17/3417
See application file for complete search history.

(56) References Cited

U.S. PATENT DOCUMENTS

| | | | |
|---|---|---|---|
| 6,077,248 A | | 6/2000 | Zumschlinge |
| 6,217,557 B1* | | 4/2001 | Håkansson ........ A61B 17/3415 604/158 |
| 6,537,205 B1* | | 3/2003 | Smith .................... A61B 1/015 600/104 |
| 6,609,020 B2* | | 8/2003 | Gill ........................ A61B 90/11 600/423 |
| 7,691,087 B2* | | 4/2010 | Gough ............... A61B 5/14546 604/165.01 |
| 8,128,600 B2* | | 3/2012 | Gill ........................ A61M 25/00 604/175 |
| 2008/0262431 A1 | | 10/2008 | Anderson et al. |
| 2009/0234227 A1 | | 9/2009 | Punga |
| 2010/0130937 A1* | | 5/2010 | Voss .................. A61M 25/0017 604/164.03 |
| 2010/0318061 A1* | | 12/2010 | Derrick ................. A61L 29/106 604/508 |
| 2015/0011938 A1* | | 1/2015 | Gill .................... A61B 17/3415 604/151 |

FOREIGN PATENT DOCUMENTS

| | | |
|---|---|---|
| WO | 03/077785 A1 | 9/2003 |
| WO | 2007/133776 A2 | 11/2007 |
| WO | 2008/020241 A2 | 2/2008 |
| WO | 2013/127884 A1 | 9/2013 |

OTHER PUBLICATIONS

Jun. 15, 2015 Written Opinion issued in International Patent Application No. PCT/GB2015/050798.

Sep. 25, 2014 Search Report issued in British Patent Application No. 1404978.7.

* cited by examiner

NEUROSURGICAL APPARATUS

The present invention relates to improved neurosurgical apparatus, in particular to neurosurgical apparatus comprising a plurality of tubes for insertion into the brain.

Neurosurgical catheters for insertion into the brain parenchyma through a hole in the skull are known. For example, WO03/077785 describes a fine catheter that can be used to deliver a therapeutic agent to an accurately defined target site within the brain. The technique described in WO03/077785 comprises firstly implanting a guide tube using a stereotactic procedure that ensures the distal end of the guide tube is accurately located at a position just short of the desired brain target. After implantation of the guide tube, the fine catheter is guided along the lumen of the guide tube until the catheter tip reaches the target site. Therapeutic agent is then delivered to the target site through the catheter. WO2008/020241 describes a three tube variant of such a guide tube based system.

Guide tube based solutions of the type described in WO03/077785 and WO2008/020241 allow fine catheters to be very accurately guided to targets within the brain. It has, however, been found by the present inventors that inserting a pre-primed catheter (e.g. a catheter already filled with inert liquid) into a previously implanted guide tube can result in any air or liquid that is present within the lumen of the previously implanted guide tube being driven into the brain. In particular, it has been found that in certain instances the insertion of a catheter into a previously implanted guide tube can cause a bubble or bubbles of air to form at or around the catheter tip. Such air bubbles can be detrimental to delivering a uniform and predictable distribution of fluid into the brain through the catheter.

According to a first aspect of the present invention, neurosurgical apparatus is provided that comprises a guidance device comprising a guide tube, and a neurosurgical instrument for insertion into the guide tube, wherein, when the neurosurgical instrument is being inserted into the guide tube, the inner surface of the guide tube at least partially engages the outer surface of the neurosurgical instrument thereby guiding the neurosurgical instrument along a predefined path through the guide tube, characterised in that at least one of the guidance device and the outer surface of the neurosurgical instrument are configured to provide a fluid return path for carrying any fluid displaced from within the guide tube during insertion of the neurosurgical instrument into the guide tube.

The neurosurgical apparatus of the present invention thus comprises a neurosurgical instrument (e.g. a catheter or electrode) in combination with a guidance device that includes a guide tube. The guide tube has an inner surface that defines a lumen or channel for receiving the neurosurgical instrument. The neurosurgical instrument and guide tube are configured such that the neurosurgical instrument can be inserted into the guide tube. In particular, the inner surface of the guide tube and the outer surface of the neurosurgical device are arranged to at least partially engage each other so that the guide tube acts to guide the neurosurgical instrument along a predefined path or trajectory within the guide tube during insertion. As mentioned above in connection with prior art devices, the guide tube may be implanted in a subject using high precision stereotactic techniques or with a surgical robot. The guidance of the neurosurgical instrument along a predetermined path within the guide tube thus ensures the neurosurgical instrument is passed along the trajectory required for it to reach its target site in the brain.

As mentioned above, it is known to insert a neurosurgical instrument (e.g. a catheter or electrode) into the brain through a previously implanted guide tube. The present inventors have, however, found that inserting a primed catheter (e.g. a catheter already filled with inert liquid) into a previously implanted guide tube will often drive any fluid that is present within the guide tube along the guide tube and into the brain. This action can be considered a piston type effect where the close fitting catheter and guide tube form a seal such that insertion of the catheter into the proximal end of the guide tube forces fluid present in the guide tube out of the distal end of the guide tube. If the guide tube contains any air bubbles, these typically enter the brain and congregate to form a large air bubble near the distal end of the guide tube. This air bubble has been found to affect how any fluid that is subsequently expelled from the catheter distributes within the brain. In particular, the predictable fluid distribution (e.g. via convection enhanced delivery) that occurs in the absence of such an air bubble is disrupted and treatment efficacy may be reduced.

In accordance with the present invention, at least one of the guidance device (e.g. the guide tube) and the outer surface of the neurosurgical instrument are configured to provide a fluid return path for carrying any fluid (e.g. liquid and/or gas) displaced from within the guide tube during insertion of the neurosurgical instrument into the guide tube. As explained below, the fluid return path may be provided in several ways. For example, a fluid return path may be provided by adapting the cross-sectional profile of the outer surface of the neurosurgical instrument and/or by adapting the cross-sectional profile of the inner surface of the guide tube of the guidance device.

The fluid return path of the present invention thus provides a route or conduit for carrying away fluid that is displaced by the action of inserting the neurosurgical instrument into the guide tube. In particular, the fluid return path provides an alternative path for fluid that is displaced during the insertion process that prevents at least some of the displaced fluid being expelled from the distal end of the guide tube into the brain. The return fluid path thus provides a route for displaced fluid to be carried away from the brain. As explained below, the fluid is preferably returned in a direction that opposes the direction of neurosurgical instrument insertion (e.g. the returned fluid preferably flows in substantially the opposite direction to the direction of neurosurgical instrument insertion). Conveniently, the fluid return path removes fluid from the implantation site to a different location which may be inside or outside of the body. The displaced fluid that passes along the fluid path preferably does not enter the brain and is conveniently vented to outside of the skull. For example, returned fluid may be expelled from a vent or aperture located at or in the vicinity of the proximal end of the guide tube.

The provision of such a fluid return path in accordance with the present invention has the advantage of reducing the amount of unwanted liquid or air that is driven into brain during insertion of a neurosurgical instrument through a previously implanted guide tube. This is particularly advantageous when the neurosurgical instrument is a catheter because it prevents unwanted air bubbles forming near the target site that can affect the distribution of delivered therapeutic liquids. The apparatus of the present invention thus improves fluid distribution and can thereby enhance treatment efficacy.

The fluid return path may be provided in a variety of ways, whilst still ensuring the guide tube performs the task of guiding the neurosurgical instrument along a predefined path. In a preferred embodiment, the fluid return path is provided by appropriately configuring the relative cross-sectional profiles of the outer surface of the neurosurgical instrument and the inner surface of the guide tube. In particular, the inner surface of the guide tube and the outer surface of the neurosurgical instrument preferably have cross-sectional profiles that are configured to provide, when the neurosurgical instrument is inserted into the guide tube, at least one conduit that provides the fluid return path. In other words, the inner surface of the guide tube and/or the outer surface of the neurosurgical instrument may be profiled so that, when the neurosurgical instrument is inserted into the guide tube, there is a gap between the neurosurgical instrument and the guide tube that runs along some or all of the length of the guide tube. This gap can thus provide the one or more conduits that form the fluid return path.

Advantageously, the inner surface of the guide tube is profiled. For example, rather than having a circular cross-section, the inner surface of the guide tube may be profiled. The inner surface of the guide tube may include slots, slits, protrusions or recesses as appropriate. The profile of the inner surface of the guide tube may thus provide the at least one fluid conduit when a neurosurgical instrument (e.g. having an outer surface with a circular cross-section) is inserted into the guide tube.

Although the inner surface of the guide tube may be profiled, it still performs the function of engaging the neurosurgical instrument so that the neurosurgical instrument passes along the predetermined path. In a preferred embodiment, the inner surface of the guide tube has a cross-sectional profile that comprises a plurality of circumferentially spaced apart guidance regions for contacting the neurosurgical instrument. At least two, at least three, at least four or at least five circumferentially spaced apart guidance regions may be provided for contacting the neurosurgical instrument. The guidance regions may be circumferentially separated from each other by one or more spacer regions where there is no contact between the guide tube and the neurosurgical instrument. The guidance regions may thus be lobes that project inwardly from the inner surface of the guide tube wall. The guidance regions are preferably arranged to contact the inserted neurosurgical instrument and thereby define the location of the instrument relative to the guide tube.

The above described guidance regions may be inwardly projecting ribs or ridges that run along the entire length of the inner surface of the guide tube. Advantageously, the guidance regions may be inwardly projecting ribs or ridges that run along at least some of the length of the inner surface of the guide tube. In particular, the ribs or ridges may run along only a part of the length of the inner surface of the guide tube. For example, the ribs or ridges may be provided along up to 90%, 80% or 70% of the length of guide tube. Advantageously, the ribs or ridges may only be provided at the distal end of the guide tube. The guidance regions may comprise projections from the inner surface of the guide tube towards the central longitudinal axis of the guide tube. Conduits forming the return fluid path may be provided by the spacer regions between the guidance regions. The guidance regions may be spaced in any arrangement, but are preferably equally circumferentially spaced apart from each other. Conveniently, the inner surface of the guide tube has a cross-sectional profile that comprises three circumferentially spaced guidance regions for contacting the neurosurgical instrument. These three guidance regions may be spaced 120° apart from each other around the circumference of the guide tube. The inner surface of the guide tube may, in a preferred embodiment, have a cross-sectional profile having the form of a clover leaf.

The provision of a plurality of circumferentially spaced guidance regions that contact the neurosurgical instrument provides the necessary guidance to the neurosurgical instrument when it is inserted into the guide tube. In particular, the guidance regions allow motion of the neurosurgical instrument along the predefined path (e.g. motion of the neurosurgical instrument along a predefined path parallel to the longitudinal axis of the guide tube) but prevent any substantial motion of the neurosurgical instrument in the plane perpendicular to the predefined path. The use of three guidance regions, for example in a clover leaf type of arrangement, ensures the neurosurgical instrument is located centrally within the lumen of the guide tube. The guide tube may comprise rigid material that does not deform during insertion of the neurosurgical instrument. Preferably, the guide tube comprises flexible material, such as plastic, to permit some deformation of the guide tube during insertion of the neurosurgical instrument. Providing three, equally circumferentially spaced, guidance regions helps ensure any such deformations do not affect the central location of the neurosurgical instrument within the guide tube. The neurosurgical instrument passed through the guide tube may be rigid (e.g. a stiff tube) or flexible.

The outer surface of the neurosurgical instrument preferably has a substantially circular cross-section. The neurosurgical instrument may thus be a catheter of standard type and the guide tube may be adapted to provide the fluid return path when used with such a catheter. The fluid return path may then be provided by appropriately profiling the inner surface of the guide tube. In other words, the inner surface of the guide tube may be profiled to provide one or more fluid conduits on insertion of a neurosurgical instrument having an outer surface with a substantially circular cross-section. For example, the inner surface of the guide tube may be configured to have a non-circular cross-sectional profile (e.g. it may have an oval or square cross-section) such that fluid conduits are formed between the guide tube and the neurosurgical instrument. These fluid conduits may be formed by the guide tube comprising slots, slits or spaced apart guidance regions as described above.

Instead of, or in addition to, adapting the inner surface of the guide tube it is also possible to appropriately adapt or modify the cross-sectional profile of the outer surface of the neurosurgical instrument. For example, the neurosurgical instrument may have an outer surface with a non-circular cross-sectional profile (e.g. it may have an oval, square, cloverleaf or irregularly shaped cross-section). The outer surface of the neurosurgical instrument may have a cross-sectional profile that comprises a plurality of protrusions. For example, a plurality of protruding ribs or ridges may be provided on the outer surface of the neurosurgical instrument. If the inner surface of the guide tube has a substantially circular cross-section, then one or more gaps or conduits will be formed on insertion of a neurosurgical instrument with an outer surface having such a non-circular cross-sectional profile. It would, of course, be possible to shape the cross-sectional profiles of the outer and inner surfaces of the neurosurgical instrument and guide tube respectively in many different ways so that at least one gap or conduit is provided that forms the fluid return path.

The neurosurgical instrument is preferably elongate and thin. For example, the neurosurgical instrument may comprise a catheter or electrode that is at least 1 cm long, more preferably at least 3 cm centimetres long, or more preferably at least 5 cm centimetres long. The outer diameter (OD) of the neurosurgical instrument may be less than 2 mm, but is preferably less than 1 mm and more preferably less than 0.7 mm. The neurosurgical instrument may thus have a central longitudinal axis. For the case of a neurosurgical instrument in the form of a catheter having a circular cross-section, this central longitudinal axis would extend along the centre of the lumen of the catheter. The neurosurgical instrument may be rigid (stiff) or flexible, as required.

The guide tube is also preferably elongate. For example, it may comprise an elongate tube. The guide tube is preferably at least 1 cm long, more preferably at least 3 cm centimetres long, or more preferably at least 5 cm centimetres long. The guide tube may be shorter than the neurosurgical instrument to allow the distal end of the neurosurgical instrument to pass completely through the guide tube and into the brain. The guide tube preferably has an internal diameter (ID) appropriately matched to the neurosurgical instrument. The ID of the guide tube may be less than 2 mm, but is preferably less than 1 mm and more preferably less than 0.7 mm. The guide tube may thus have central longitudinal axis. The central longitudinal axis of the guide tube extends along the centre of the lumen or channel of the guide tube. The guide tube may be rigid (stiff) or flexible, as required.

As outlined above, the inner surface of the guide tube at least partially engages the outer surface of the neurosurgical instrument thereby guiding the neurosurgical instrument along a predefined path through the guide tube. The guide tube is therefore not an arbitrarily dimensioned tube, but is provided to guide the neurosurgical instrument along a predefined path. Advantageously, when the neurosurgical instrument is inserted into the guide tube, the central longitudinal axis of the neurosurgical instrument substantially coincides with the central longitudinal axis of the guide tube. If the guide tube comprises one or more guidance regions as described above, such guidance regions may ensure that the central longitudinal axis of the neurosurgical instrument is held so as to coincide with the central longitudinal axis of the guide tube. The guide tube thus preferably locates the neurosurgical instrument centrally within the guide tube but it would, of course, also be possible to provide off-centre alignment if desired.

The guidance device of the apparatus of the invention includes a guide tube and may optionally include further components. These further components may include screws, clips, attachment devices etc. The guidance device may also comprise at least one additional tube (i.e. a tube in addition to the guide tube). For example, an additional tube may be provided that runs parallel to the guide tube and is in fluid communication with the lumen at the distal end of the guide tube to provide the fluid return path.

The guidance device may consist only of a guide tube. A guide tube may be provided that has a head at its proximal end for attachment to the skull of a subject. Advantageously, the guidance device further comprises an outermost tube. The guide tube is conveniently insertable into the outermost tube. The outermost tube may have an inner surface with a substantially circular cross-section. The outer surface of the guide tube may also have a substantially circular cross-section and be dimensioned to fit snugly within the outermost tube. The outermost tube may have a head at its proximal end for attachment to a hole formed in the skull of a patient (e.g. the head may include ridges or protrusions that allow it to be fixed within a hole formed in the skull). The guide tube may comprise a feature at its proximal end for securing the proximal end of the guide tube to the head of the outermost tube. The guide tube may, for example, clip into the outermost tube when fully inserted.

In use, the outermost tube may be firstly implanted in the head of the subject using guided surgery techniques (e.g. using a stereotactic frame or surgical robot). The guide tube may then be inserted into the outermost tube. This insertion may be performed by hand because the guide tube will be guided along the required trajectory by the outermost tube. The distal end of the guide tube may protrude from the end of the outermost tube when fully inserted, or it may be terminate within the outermost tube. The proximal end of the guide tube may, when fully inserted, clip into engagement with the head of the outermost tube. It should be noted that, during this guide tube insertion process, any fluid (e.g. gas/air) within the lumen of the outermost tube can escape from the brain via the open lumen of the guide tube. The insertion of the guide tube into the outermost tube does not therefore result in any significant volumes of fluid being forced into the brain. It should be noted that it would also be possible to provide an outer fluid return path between the outermost tube and the guide tube; for example, the inner surface of the outermost tube may have a non-circular cross-sectional profile (e.g. a cloverleaf profile) that provides an outer fluid conduit when a guide tube is inserted therein. This option may be desirable if, for example, the guide tube lumen is occluded during insertion (e.g. if an internal stiffening rod or wire is placed in the guide tube lumen during insertion into the outermost tube).

Once the guide tube is inserted into the patient (e.g. retained in the outermost tube), the neurosurgical instrument is inserted into the guide tube. In the case of the neurosurgical instrument being a catheter, the catheter may be pre-primed (e.g. filled with inert liquid) prior to insertion. The catheter may also be connected to a fluid pump during insertion so that there is a continual expulsion of liquid from the catheter tip. As the pre-primed catheter is inserted into the guide tube, any fluid within the guide tube (e.g. a mixture of liquid and air that may include liquid expelled from the catheter tip) is routed along the return fluid path. This prevents such fluid being driven into the brain during catheter insertion.

The distal end (tip) of the neurosurgical instrument is preferably configured to protrude from the distal end of the guide tube. If an outermost tube is provided, the neurosurgical instrument may not protrude from the distal end of the outermost tube (i.e. it may remain located within the outermost tube). If an outermost tube is provided, the distal end (tip) of the neurosurgical instrument is preferably configured to protrude from the distal end of the outermost tube. Preferably, the neurosurgical instrument protrudes at least 1 cm, at least 2 cm or at least 3 m from the distal end of the guidance device. Preferably, the neurosurgical instrument protrudes no more than 15 cm, no more than 10 cm, or no more than 5 cm from the distal end of the guidance device. The distal end of the neurosurgical instrument may not protrude at all from the guidance device (e.g. the tip of the neurosurgical instrument may be arranged to be flush or sub-flush to the distal end of the guidance device).

The neurosurgical instrument preferably includes a stop (e.g. a hub with a tapered or flat surface) to set the depth of insertion. The stop may comprise any suitable feature that limits the insertion or travel of the neurosurgical instrument into the guidance device. The stop of the neurosurgical instrument may engage a feature of the guidance device. For example, the proximal end of the guidance device (e.g. the proximal end of the guide tube or of an outermost tube, if present) may include a feature that engages the stop of the neurosurgical instrument. In this manner, the neurosurgical instrument and guidance device act together in a way that controls the insertion depth of the neurosurgical instrument into the brain.

As explained above, the fluid return path may be provided by a conduit between the neurosurgical instrument and the guide tube. The conduit may extend along the whole of the length of the guide tube, or the conduit may extend along only a part of the length of the guide tube. In other words, the conduit preferably extends at least partially along the length of the guide tube.

During insertion of the neurosurgical instrument into the guide tube, the conduit acts as a path for fluid displaced from within the guide tube. Advantageously, the apparatus comprises a seal for sealing the fluid return path. In other words, a sealing means may be provided for occluding (i.e. blocking) the fluid return path. A fluid tight seal of the conduit(s) forming the fluid return path can thus be advantageously provided. In one example, the apparatus may be arranged so that the fluid return path is blocked or sealed when the neurosurgical instrument is fully inserted into the guide tube. In other words, the seal may cause the fluid return path to be blocked when the neurosurgical instrument is fully inserted into the guide tube.

Engagement of a stop on the catheter with a feature on the guide tube (or outermost tube, if present) may provide the seal that seals (i.e. blocks) the fluid return path. In this manner, displaced fluid can be carried away from the brain during neurosurgical instrument insertion but the fluid return path may be sealed afterwards (e.g. by virtue of the seal) to prevent it providing a route for infection to enter the brain or for unwanted drainage of fluid from the brain. The fluid return path thus allows return of fluid during the act of neurosurgical instrument insertion, but preferably prevents fluid return when the neurosurgical instrument is fully inserted into the guide tube.

The neurosurgical instrument may comprise any instrument that can be inserted directly into the brain parenchyma. The neurosurgical instrument may comprise an electrode. The neurosurgical instrument may comprise a neurosurgical catheter. The catheter may be a neurosurgical or intracranial catheter suitable for delivering fluid into the brain by convection enhanced delivery. The catheter may include one or more apertures at its distal end for dispensing a liquid. Preferably, the catheter comprises a single aperture at its distal end. The catheter preferably comprises a fine tube. The fine tube preferably has an outer diameter of less than 1 mm, or more preferably less than 0.7 mm. The fine tube may have regions of different outer diameter. For example, the distal end of the fine tube may have a smaller outer diameter than the proximal end of the fine tube. In other words, the proximal end of the fine tube may have a larger diameter than the distal end. This can reduce buckling during insertion of the catheter into the guide tube. Any change in outer diameter of the fine tube may be tapered. The apparatus may be arranged to deliver liquid using convection enhanced delivery. The liquid delivered by the catheter may comprise a therapeutic agent. The catheter may be connected to a pump; the pump may be an external pump assembly or an internally (subcutaneously) implanted pump. The neurosurgical catheter may be connected to a percutaneous port or subcutaneous port. Advantageously, the neurosurgical catheter may be pre-filled with liquid prior to insertion into the guide tube.

The apparatus of the present invention may be formed from any suitable material. Advantageously, at least one of the neurosurgical catheter and the guidance device comprise plastic material. The plastic may comprise polyurethane (e.g. Carbothane). The neurosurgical instrument and/or the guide tube may be formed by a moulding or extrusion process. The present invention thus also extends to a method of making such a guide tube or neurosurgical instrument by an extrusion and/or moulding process.

According to a further aspect of the invention, a guide tube is provided that comprises an inner surface having a cross-sectional profile that defines a plurality of circumferentially spaced apart guidance regions for contacting a neurosurgical instrument. The cross-sectional profile that defines a plurality of circumferentially spaced apart guidance regions may extend along at least a part of the length of the guide tube. The guide tube may also include a head for attachment to the skull. A guide tube may thus be provided that comprises a lumen for guiding neurosurgical instruments, the internal surface of the lumen having a cross-sectional profile that comprises a plurality of lobes that project towards the central axis of the lumen. Preferably, three circumferentially spaced apart guidance regions are provided (e.g. in a clover leaf arrangement). These guidance regions may extend along the whole length of the guide tube or only along a part of the length of the guide tube. The guide tube is preferably provided in combination with a catheter. The external surface of the catheter preferably has a circular cross-sectional profile. Advantageously, the dimensions of the guide tube and catheter are configured so that the guidance regions engage and guide the catheter as it is inserted into the guide tube. Further preferred features of the guide tube and catheter are described above.

According to a further aspect of the invention, neurosurgical apparatus is provided that comprises a first tubular member and a second tubular member. The first tubular member preferably comprises an inner surface that defines a channel along which the second tubular member can be passed. Advantageously, the inner surface of the first tubular member and the outer surface of the second tubular member are configured to provide at least one fluid conduit between the first tubular member and the second tubular member. The apparatus may also comprise a seal for blocking the at least one fluid conduit when the second tubular member is fully inserted into the first tubular member. Conveniently, the cross-sectional profile of the inner surface of the first tubular member has a different shape to the cross-sectional profile of the outer surface of the second tubular member. A third tubular member may also be provided. The second tubular member preferably comprises an inner surface that defines a channel along which the third tubular member can be passed. Advantageously, the inner surface of the second tubular member and the outer surface of the third tubular member are configured to provide at least one fluid conduit between the second tubular member and the third tubular member. Conveniently, the cross-sectional profile of the inner surface of the second tubular member has a different shape to the cross-sectional profile of the outer surface of the third tubular member.

In a further aspect, the present invention provides a neurosurgical guide tube comprising a lumen for guiding neurosurgical instruments, wherein the internal surface defining the lumen has a non-circular cross-sectional profile. A neurosurgical instrument having an outer surface with a circular cross-sectional profile may be used in combination with such a guide tube.

In a further aspect, the present invention provides a neurosurgical catheter for insertion into the brain via a guide tube, wherein the external surface of the neurosurgical catheter has a non-circular cross-sectional profile. A guide tube comprising an internal surface defining a lumen having a circular cross-sectional profile may be used in combination with such a catheter.

In a further aspect, the present invention provides neurosurgical apparatus comprising a guide tube having a proximal end and a distal end. A catheter may also be provided that has a lumen filled with a liquid. The inner surface of the guide tube and the outer surface of the catheter preferably have cross-sectional profiles that provide guidance of the catheter when inserted into the guide tube. The cross-sectional profiles preferably also define one or more gaps that act as one or more conduits for carrying fluid from within the guide tube. These one or more conduits conveniently guide fluid to the proximal end of the guide tube during insertion of the catheter into the guide tube.

The present invention also extends to methods of using the apparatus. Such a method may comprise the steps of inserting the guidance device into the brain. The neurosurgical instrument may then be passed through the guide device and into the brain. The apparatus may also be used for delivery of therapeutic agent to the brain (e.g. using a neurosurgical instrument in the form of a catheter).

The invention will now be described, by way of example only, with reference to the accompanying drawings in which.

Figure 1:
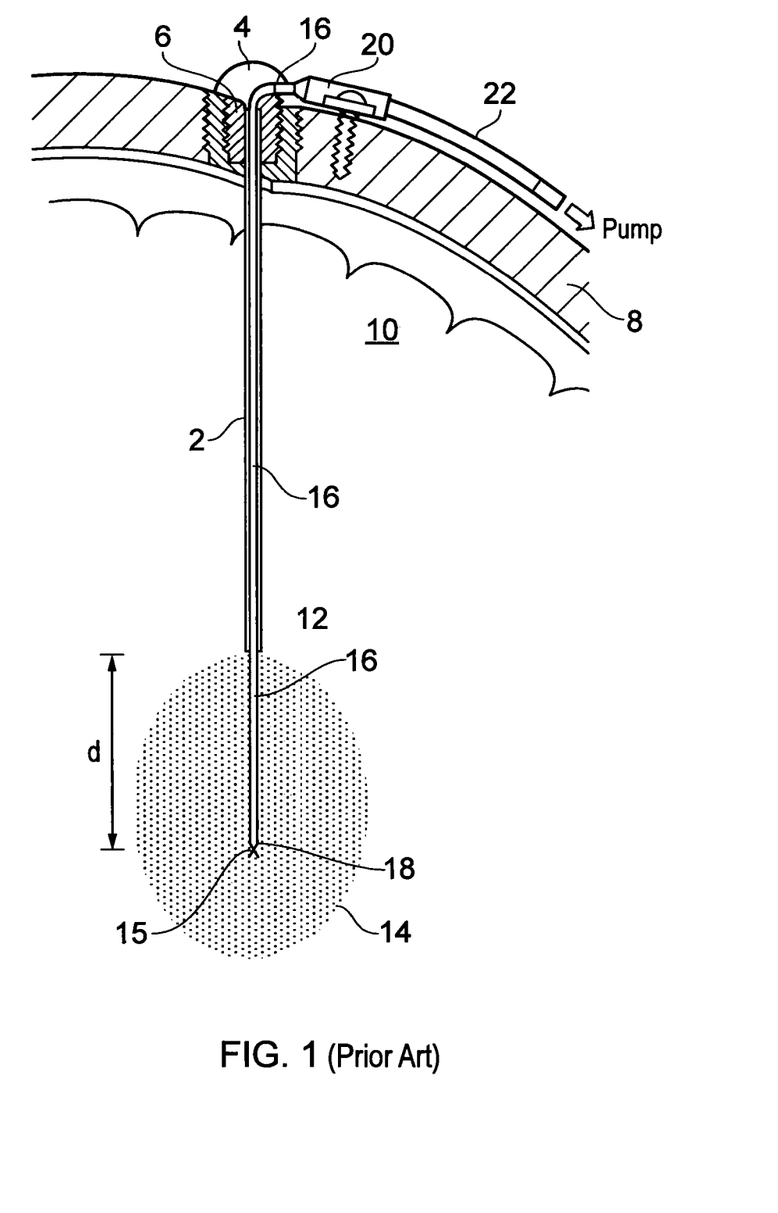
FIG. 1 shows a prior art guide tube and catheter system.

Referring to FIG. 1, a prior art implanted fluid delivery system of the type described in WO2003/077785 is illustrated.

The fluid delivery system comprises a guide tube comprising an elongate tube 2 having a head 4 at its proximal end. The head 4 has an external thread 6 to allow attachment to a burr hole formed in the skull bone 8 of a subject. The guide tube is inserted stereotactically into the brain parenchyma 10 using a stereoguide device. In particular, the guide device can be accurately inserted in the brain along a predefined axis of insertion such that it's distal end 12 is located just short (by a distance d) of a target point 15.

After the guide tube has been implanted, a flexible catheter is inserted through the head 4 and into the tube 2. The flexible catheter comprises a length of fine tubing 16 having an outside diameter of 1 mm or less. During implantation, the fine tubing 16 of the catheter is inserted into the guide device 2 and advanced therethrough until the distal end 18 of the fine tube 16 protrudes a distance "d" from the distal end 12 of the tube 2 and thereby reaches the target point 15. The inner diameter of the tube 2 is slightly larger than the outer diameter of the fine tubing 16 of the catheter to provide the required catheter guidance.

The fine tube 16 of the catheter is connected to a hub 20 that is screwed to the outside of the skull 8. A supply or connector tube 22 is in fluid communication with the fine tube 16 via a channel formed in the hub 20. The supply tube 22 may receive fluid from a remotely located drug pump, which is then routed along the fine tube 16 of the catheter to the target volume 14.

To prevent air being expelled from the catheter when fluid delivery is initiated using apparatus of the type described in WO2003/077785, the catheter can be delivered after being primed with inert fluid. It has, however, been found by the present inventors that the act of inserting the catheter into the guide tube can drive any fluid present within the guide tube (typically a mix of liquid and air bubbles) into the brain. This occurs because the catheter effective acts as a piston which drives fluid out of the distal end of the elongate tube 2 of the guide tube. If the guide tube contains air, it can form an air bubble in the brain at the distal end of the guide tube which has been found to affect the distribution of fluid subsequently expelled from the catheter tip.

Figure 2A:
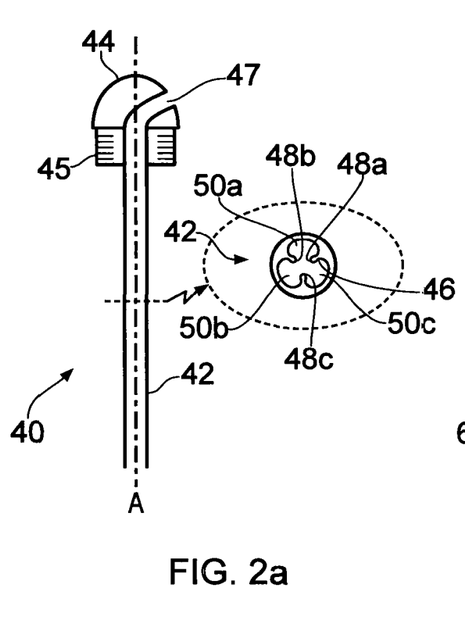
FIGS. 2a-2c show neurosurgical apparatus of the present invention.
Figure 2B:
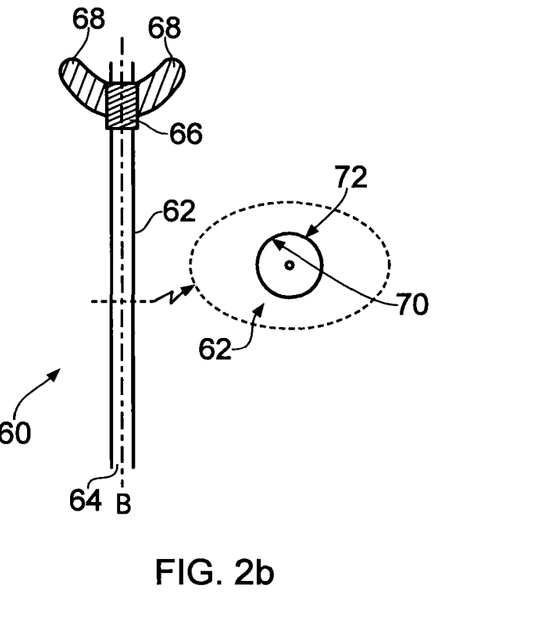
Figure 2C:
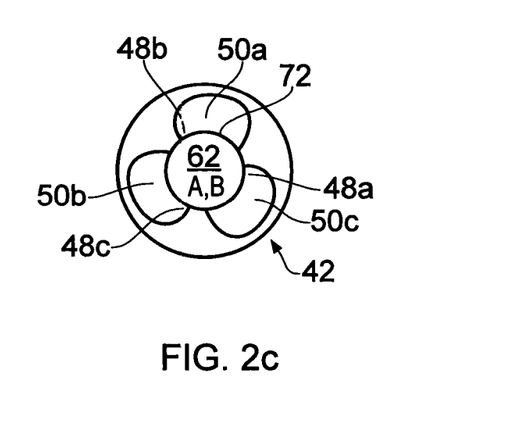

Referring to FIGS. 2a to 2c, neurosurgical apparatus in accordance with the present invention that comprises a guide tube and catheter is illustrated.

FIG. 2a illustrates a guidance device 40 comprising an elongate guide tube 42 with a head 44 attached to its proximal end. The outside of the head 44 includes a screw-threaded portion 45 that allows the guide tube 42 to be secured to a hole formed in the skull of a subject. A slot or inlet 47 formed in the domed upper surface of the head 44 provides access to the lumen of the guide tube 42. The axis along which the guide tube is inserted may be accurately defined using a known stereotactic or robot based insertion procedure.

A cross-section through the guide tube 42 is shown in the inset to FIG. 2a. The outer surface of the guide tube 42 has a circular cross-sectional profile. In accordance with the present invention, the inner surface 46 of the guide tube 42 that defines the lumen of the tube is profiled. In particular, the inner surface 46 of the guide tube has a cross-sectional profile that comprises three guidance regions 48a, 48b and 48c (referred to collectively as guidance regions 48) that each protrude towards the central longitudinal axis A of the guide tube 42. The three guidance regions 48 are spaced apart from each other by approximately 120° and are separated by gaps 50a, 50b and 50c (referred to collectively as gaps 50). The form of this cross-sectional profile is similar to the shape of a clover leaf. The guidance regions 48 are ridges or protrusions that, in this example, extend the entire length of the guide tube 42. It would, however, be possible for the guidance regions to extend only along part of the guide tube or for the cross-sectional profile to vary along the tube (e.g. in a spiral manner). The guide tube is formed from plastic material (e.g. Carbothane) and the required inner/outer surface profiles are generated using an extrusion fabrication process. The skilled person would appreciate that it would also be possible to make the guide tube 42 from a rigid material or from two or more different materials (e.g. from a combination of soft and rigid materials).

FIG. 2b shows a catheter 60 for use in combination with the guide tube illustrated in FIG. 2a. The catheter 60 comprises a length of fine tube 62 that has a fluid dispensing aperture 64 at its distal end (tip). The proximal end of the catheter 60 comprises a hub 66 comprising a pair of wings 68. The hub 66 acts as depth stop that defines how far the fine tube 62 can be inserted into the associated guidance device 40 and the wings 68 allow the catheter to be secured to the skull (e.g. using bone screws). The inset to FIG. 2b shows a cross-section through the fine tube 62. It can be seen that the inner surface 70 and the outer surface 72 of the fine tube 62 have substantially circular cross-sections.

In use, the fine tube 62 of the catheter 60 is inserted into the lumen of the guide tube 42 of the guidance device 40 through the inlet 47 of the head 44. The fine tube 62 is primed (filled) with an inert liquid prior to insertion. The primed fine tube 62 is then pushed into guidance device 40 until the hub 66 of the catheter engages the head 44 of the guidance device. The hub 66 thus acts as a depth setting feature or stop that defines how far the fine tube 62 of the catheter 60 can be inserted into the guide tube 42. The inner surface 46 of the guide tube 42 is dimensioned so that the guidance regions 48 engage the outer surface 72 of the fine tube 62 of the catheter 60; this may involves a small amount of elastic deformation of the guide tube 42 and/or fine tube 62. The three guidance regions 48a-48c thus act to engage and retain the catheter centrally within the guide tube 42. In this example, the central longitudinal axis A of the guide tube 42 is arranged to coincide with the central longitudinal axis B of the fine tube 62. The fine tube 62 is thus free to be inserted (and withdrawn) from the guide tube 42, but when being inserted (or withdrawn) it is guided along a predefined path through the guide tube 42. The guide tube thus performs the task of guiding the catheter to the desired target. After implantation, the apparatus can be used to deliver fluid (e.g. liquid containing therapeutic agent) to the brain. The flow rate and duration of fluid delivery will be set according to the relevant clinical requirements. The fluid delivery may comprise convection enhanced delivery (CED) and/or intermittent, bolus or chronic delivery.

It should be noted that it has been proposed previously in WO2008/020241 to provide a loose fit between a guide tube and a catheter so that a space between these two tubes fills with fluid. This, however, is achieved by altering the inner and outer diameters of circular cross-section tubes which means that the accuracy of the guidance provided by such configurations can be reduced. In the present invention, the inner surface of the guide tube at least partially engages the outer surface of the catheter and thus acts to guide the catheter along a predefined path. There is no such guidance in the arrangement described in WO2008/020241.

In addition to providing the necessary guidance, the cross-sectional profile of the inner surface 46 of the guide tube 42 defines three gaps 50a-50c when the fine tube 62 of the catheter 60 is inserted therein. This is shown in FIG. 2c. The gaps 50a-50c act as conduits that allow any fluid present in the guide tube 42 to return back up the guide tube 42 and be expelled from the inlet 47 of the head 44. The conduits defined by the gaps 50a-50c thus provide a fluid return path, such that when a catheter is inserted into the guide tube 42 a reduced amount of the fluid present in the guide tube is driven into the brain. As explained above, the fluid contained within the guide tube 42 is typically a mixture of liquid (e.g. cerebrospinal fluid) and air. In the absence of the fluid return path, it has been found that this fluid is driven out of the distal end of the guide tube and into the brain. The presence of air bubbles in the brain in the vicinity of the region where liquid (e.g. containing therapeutic agent) is to be dispensed can lead to uneven and unpredictable fluid distribution. The present invention helps to overcome this problem.

Instead of adapting the profile of the inner surface of the guide tube to provide conduits, it would also be possible to suitably adapt the outer surface of a catheter.

Figure 3A:
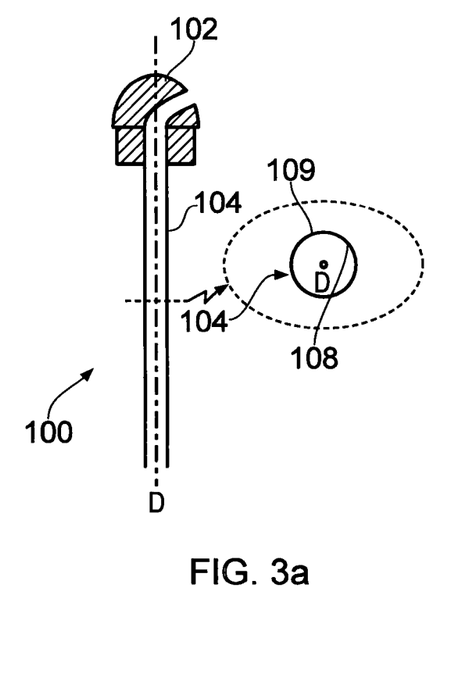
FIGS. 3a-3c show further neurosurgical apparatus of the present invention.

FIG. 3a shows a guidance device 100 that comprises a head 102 and a guide tube 104. As shown in the cross-sectional view of the inset to FIG. 3a, the guide tube 104 has a substantially circular inner surface 108 and a substantially circular outer surface 109. The guide tube 104 has a central longitudinal axis D.

Figure 3B:
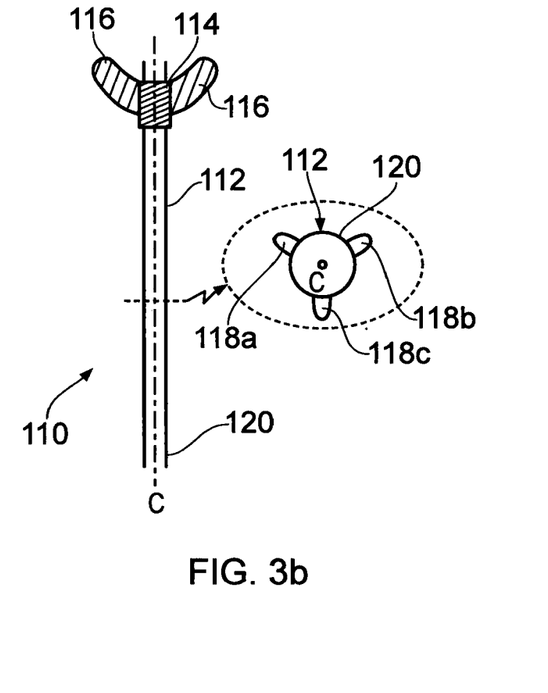

FIG. 3b shows a catheter 110 that comprises a fine tube 112 and a depth setting hub 114 with a pair of wings 116. As shown in the inset to FIG. 3b, the fine tube 112 includes three ridges or protrusions 118a-118c (collectively referred to as protrusions 118) that run along the length of its outer surface 120. The ridges 118 extended radially outwardly from the central longitudinal axis C.

Figure 3C:
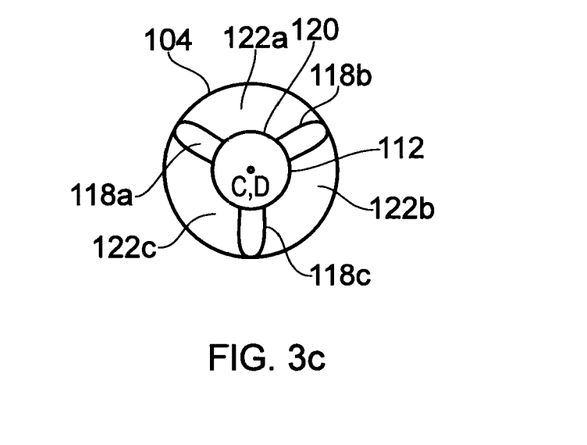

The catheter 110 is dimensioned for insertion into the guidance device 100. As shown in FIG. 3c, the protrusions 118 on the outer surface 120 of the fine tube 112 are arranged to engage the inner surface 108 of the guide tube. The central longitudinal axis C of the fine tube 112 of the catheter 110 will thus coincide with the central longitudinal axis D of the guide tube 104. The guide tube 104 thus guides the catheter 110 along a predefined (central) path when inserted therein. In addition, gaps 122a-122c are provided between the catheter 110 and the guide tube 104 that provide fluid conduits that perform the same fluid return path function as described above with reference to FIGS. 2a-2c.

It should also be noted that both the outer surface of the catheter and the inner surface of the guide tube may have non-circular profiles that provide such conduits.

Figure 4:
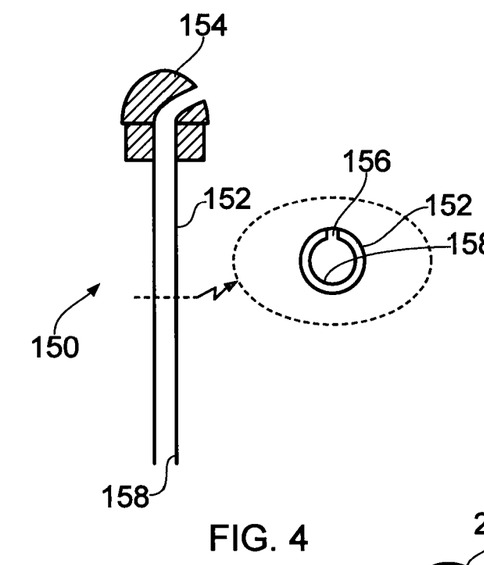
FIG. 4 shows a guide tube in accordance with the present invention comprising an internal recess or slot for providing a fluid conduit.

Referring to FIG. 4, an alternative guidance device 150 in accordance with the present invention is shown. The guidance device 150 comprises a guide tube 152 with a head 154. As shown in the inset to FIG. 4, the guide tube 152 include a slit or slot 156 that runs along the length of its inner surface 158. On insertion of a catheter with a circular cross-section into the guide tube 152, the slot 156 provides a fluid conduit that acts as a fluid return path. Although one slot 156 is shown, a plurality of slots may be provided.

Although the fluid return path may be provided by appropriately defining the cross-sectional profiles of the outer surface of the catheter and the inner surface of the guide tube to provide a gap that acts as a conduit, the fluid return path may be provided in many different ways.

Figure 5A:
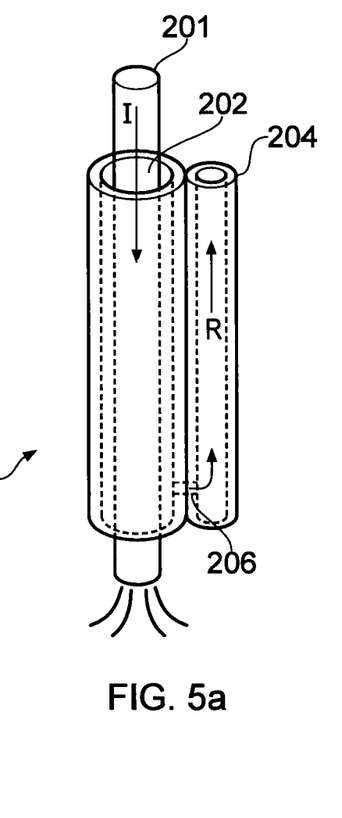
FIG. 5a shows a guide tube in accordance with the present invention that comprises two bores.

Referring to FIG. 5a, a part of a guidance device 200 is shown. The device 200 comprises a guide tube 202 for guiding a catheter 201 along a predetermined path. The device 200 may include a head for attachment to the skull, but this is not shown in FIG. 5. A secondary venting tube 204 is provided adjacent the guide tube 202. A fluid cross-link 206 is provided between the guide tube 202 and the venting tube 204 near the distal end of the guide tube 202. Insertion of a close fitting catheter 201 into the guide tube 202 along the insertion direction I, forces fluid in the guide tube 202 to the distal end of the guide tube 202 but this fluid then passes through the cross-link 206 and is returned (along direction R) by the venting tube 204. This arrangement thus also provides a fluid return path.

Figure 5B:
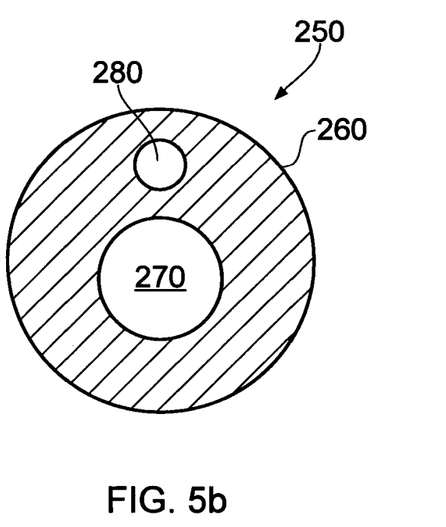
FIG. 5b shows a guide tube with a secondary bore.

FIG. 5b shows a cross-section of a guidance device 250 that can be considered a variant of the device shown in FIG. 5a. Instead of providing a guide tube and an adjacent secondary venting tube, the guidance device 250 comprises a guide tube 260 comprising an external surface with a circular cross-section. The guide tube 260 comprises a first lumen 270 for receiving and guiding a catheter and a secondary lumen 280 that provides a fluid return path. A fluid cross-link (not shown) provided at the distal end of the guide tube 260 allows, in a similar manner to that described for the apparatus of FIG. 5a, fluid from the first lumen 270 to be returned along the second lumen 280 when a neurosurgical instrument is inserted into the first lumen 270.

Figure 6:
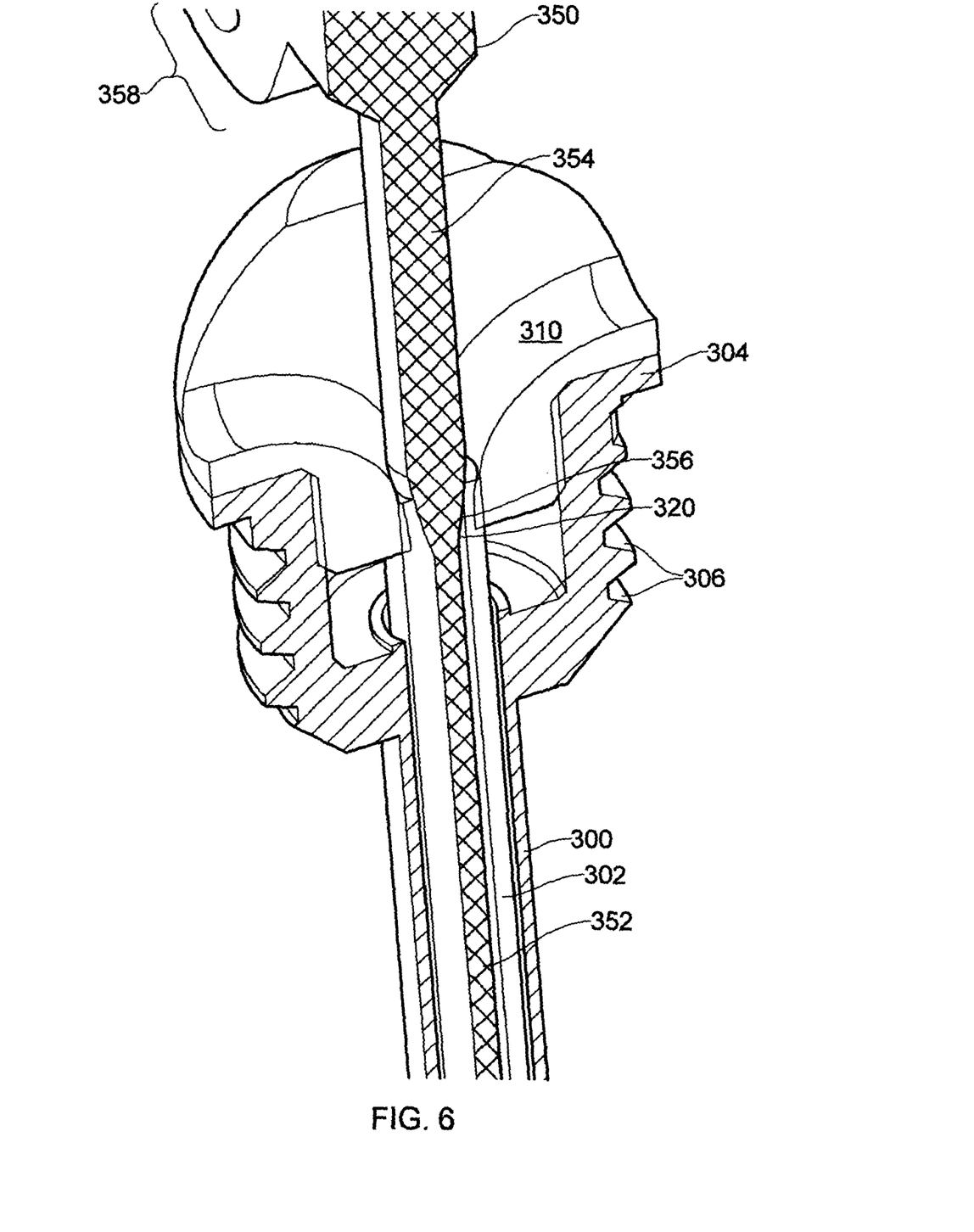
FIG. 6 shows a catheter inserted into an inner guide tube that is inserted into an outermost guide tube.

Referring to FIG. 6, further neurosurgical apparatus of the present invention is illustrated. The apparatus comprises a guidance device and a catheter 350.

The guidance device comprises an outermost guide tube 300 and an inner guide tube 302. The outermost guide tube 300 has a head 304 at its proximal end that includes a screw-threaded portion 306 that allow the outermost guide tube 300 to be secured to a hole formed in the skull of a subject. The internal surface along the length of the outermost guide tube has a substantially circular cross-section (although this internal surface could also comprise a slot or cloverleaf profile if a fluid return path between the outermost guide tube and the inner guide tube was required). The inner guide tube 302 has a head 310 at its proximal end that can be snap or press fitted into a recess formed in the head 304 of the outermost guide tube 300. The outer surface of the inner guide tube 302 has a substantially circular cross-section and is dimensioned to fit within the lumen define by the outermost guide tube. Although not illustrated in FIG. 6, the inner surface of the inner guide tube 302 has a "cloverleaf" cross-sectional profile of the type shown in FIG. 2c. A tapered opening 320 with a tapered conical profile (i.e. not a cloverleaf profile) is also provided at the proximal end of the inner guide tube.

A catheter 350 is also provided that has a fine tube 352 with an outer surface having a substantially circular cross-section. The catheter 350 also includes a connector tube 354 having a slighter larger outer diameter than the fine tube 352. A tapered region 356 is provided between the fine tube 352 and the connector tube 354. An attachment feature 358 (e.g. wings with screw holes) is also provided for securing the catheter to the skull after insertion. The fine tube 352 of the catheter 350 is dimensioned so as to fit inside and be guided by the inner guide tube 302. The cloverleaf type profile of the inner surface of the inner guide tube 302 in combination with the circular cross-section of the fine tube 352 thus provides a series of gaps or conduits that provide a fluid return path as explained above.

In use, the outermost guide tube 300 is firstly inserted into the brain of a subject through a hole formed in the skull. The guide tube 300 is inserted along a known trajectory (e.g. using stereotactic apparatus or a surgical robot) until the screw-threaded portion 306 engages and firmly secures the guide tube 300 tube within the hole formed in the skull. The inner guide tube 302 is then inserted into the outermost guide tube 300 until the head 310 of the inner guide tube 302 engages and is retained within the recess formed within the head 304 of the outermost guide tube 300. The lumen of the inner guide tube 302 provides a return path for any fluid within the guide tube during this insertion process.

The catheter 350 is then primed with liquid (e.g. insert liquid) and inserted into the inner guide tube 302. The catheter 350 is connected to a fluid pump (not shown) during this insertion procedure so that liquid is pushed though the catheter at a low flow rate to ensure it remains fully primed during insertion. The catheter 350 advanced into the inner guide tube 302 until its tapered region 356 engages the tapered opening 320 of the inner guide tube 302. Engagement of the tapered region 356 of the catheter 350 with the tapered opening 320 of the inner guide tube 302 has the effect of sealing the fluid return path. In other words, fluid can be returned along the conduits provided between outer surface of the fine tube 352 and the inner surface of the inner guide tube 302 until the tapered seal is established. The fluid return path is thus open during the majority of the catheter insertion process, but is blocked when the catheter is fully inserted. This seal thus prevents leakage of fluid from the brain after implantation of the neurosurgical apparatus, whilst still providing a fluid return path during catheter insertion. It should be noted that although a taper seal is shown in FIG. 6, such a fluid seal may of course be provided in a variety of different ways.

The examples given above outline a variety of ways in which the invention could be implemented. The skilled person would be aware of the various alternative arrangements that would be possible. The examples given above primarily describe the use of catheters, but it should be noted that any elongate neurosurgical instrument (e.g. electrodes, etc) could be inserted through the guide tube.

The invention claimed is:

1. Neurosurgical apparatus comprising:
a guidance device comprising a guide tube;
a neurosurgical catheter for insertion into the guide tube, an outer surface of the neurosurgical catheter having a substantially circular cross-section and an inner surface of the guide tube having a cross-sectional profile that comprises a plurality of guidance regions for contacting the neurosurgical catheter, the plurality of guidance regions being circumferentially spaced apart from each other by one or more spacer regions where there is no contact between the guide tube and the neurosurgical catheter; and
a seal provided between the neurosurgical catheter and the guide tube,
wherein, when the neurosurgical catheter is being inserted into the guide tube, the guidance regions of the guide tube at least partially engage the outer surface of the neurosurgical catheter thereby guiding the neurosurgical catheter along a predefined path through the guide tube,
the one or more spacer regions provide conduits that are configured to provide a fluid return path for carrying any fluid displaced from within the guide tube during insertion of the neurosurgical catheter into the guide tube,
the plurality of guidance regions and one or more spacer regions are disposed at least at a distal-most end of the guide tube, and
the seal seals the fluid return path such that a fluid tight seal is provided between the inserted neurosurgical catheter and the guide tube only after a tip of the neurosurgical catheter has passed out of the guide tube and into a brain of a subject.

2. The apparatus according to claim 1, wherein the plurality of guidance regions comprise three circumferentially spaced apart guidance regions.

3. The apparatus according to claim 2, wherein the cross-sectional profile of the inner surface of the guide tube has the form of a clover leaf.

4. The apparatus according to claim 1, wherein, when the neurosurgical catheter is inserted into the guide tube, a central longitudinal axis of the neurosurgical catheter substantially coincides with a central longitudinal axis of the guide tube.

5. The apparatus according to claim 1, wherein the guidance device comprises the guide tube and an outermost tube, the guide tube being insertable into the outermost tube.

6. The apparatus according to claim 1, wherein the guidance device includes a fixation device for affixing the guide tube to a burr hole formed in the skull of a patient.

7. The apparatus according to claim 1, wherein the seal causes the fluid return path to be blocked when the neurosurgical catheter is fully inserted into the guide tube.

8. The apparatus according to claim 1, wherein the neurosurgical catheter comprises a fine tube having an outer diameter of less than 1 mm.

9. The apparatus according to claim 8, wherein the neurosurgical catheter is pre-filled with liquid prior to insertion into the guide tube.

10. The apparatus according to claim 1, wherein at least one of the neurosurgical catheter and the guidance device comprise plastic material.

11. The apparatus according to claim 1, wherein the neurosurgical apparatus is configured such that no seal between the inserted neurosurgical catheter and the guide tube is formed until after the tip of the neurosurgical catheter has passed out of the guide tube and into the brain of the subject.

12. The apparatus according to claim 1, wherein the neurosurgical catheter is configured to protrude from the distal-most end of the guide tube by at least 1 cm.

13. The apparatus according to claim 1, wherein the neurosurgical catheter includes one or more features configured to set a depth of the neurosurgical catheter insertion.

* * * * *